United States Patent
Heumann et al.

(10) Patent No.: US 9,737,665 B2
(45) Date of Patent: Aug. 22, 2017

(54) SUPPLEMENTAL DEVICE FOR USE WITH AN INJECTION DEVICE, A METHOD OF OPERATION THEREOF, AND A COMPUTER PROGRAM FOR CONTROLLING A SUPPLEMENTAL DEVICE TO PERFORM THE METHOD

(71) Applicant: Sanofi-Aventis Deutschland GmbH, Frankfurt am Main (DE)

(72) Inventors: Gunter Heumann, Jena (DE); Gertrud Blei, Jena (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/786,121

(22) PCT Filed: Apr. 16, 2014

(86) PCT No.: PCT/EP2014/057790
§ 371 (c)(1),
(2) Date: Oct. 21, 2015

(87) PCT Pub. No.: WO2014/173775
PCT Pub. Date: Oct. 30, 2014

(65) Prior Publication Data
US 2016/0144124 A1 May 26, 2016

(30) Foreign Application Priority Data
Apr. 22, 2013 (EP) .................................. 13164760

(51) Int. Cl.
*G01J 3/46* (2006.01)
*A61M 5/315* (2006.01)
(Continued)

(52) U.S. Cl.
CPC .......... *A61M 5/31525* (2013.01); *A61M 5/24* (2013.01); *A61M 2005/3126* (2013.01);
(Continued)

(58) Field of Classification Search
CPC ...... A61M 5/315; A61M 5/3129; A61M 5/24; A61M 5/14546; A61M 2205/6063;
(Continued)

(56) References Cited

U.S. PATENT DOCUMENTS

| 5,963,333 A | 10/1999 | Walowit et al. |
| 2011/0238017 A1 | 9/2011 | Watanabe et al. |
| 2013/0072897 A1* | 3/2013 | Day .................... A61M 5/1452 604/500 |

FOREIGN PATENT DOCUMENTS

WO  2011117212 A1  9/2011

* cited by examiner

*Primary Examiner* — Abdullahi Nur
(74) *Attorney, Agent, or Firm* — McDonnell Boehnen Hulbert & Berghoff LLP

(57) ABSTRACT

A supplemental device for use with an injection device, the supplemental device comprising: a plurality of light sources each being configured to illuminate a surface portion of an injection device, in use, with light of a different wavelength; at least one sensor for generating sensor outputs indicative of the respective intensities of light of different wavelengths reflected from the surface portion; and a processor for: controlling the plurality of light sources to illuminate the surface portion with light of first to third different wavelengths; obtaining first to third values for sensor outputs corresponding to the first to third different wavelengths respectively; performing one or more calculations using at least the first and second values to provide one or more further values; and using the third value and the or each further value, but not the first and second values, to determine a property of the injection device.

16 Claims, 5 Drawing Sheets

(51) Int. Cl.
*A61M 5/24* (2006.01)
*A61M 5/31* (2006.01)

(52) U.S. Cl.
CPC . *A61M 2205/18* (2013.01); *A61M 2205/3306* (2013.01); *A61M 2205/3313* (2013.01); *A61M 2205/50* (2013.01); *A61M 2205/52* (2013.01); *A61M 2205/6081* (2013.01)

(58) Field of Classification Search
CPC ...... A61M 2005/3125; G01J 3/46; G01J 3/50; G01J 3/02
See application file for complete search history.

SUPPLEMENTAL DEVICE FOR USE WITH AN INJECTION DEVICE, A METHOD OF OPERATION THEREOF, AND A COMPUTER PROGRAM FOR CONTROLLING A SUPPLEMENTAL DEVICE TO PERFORM THE METHOD

CROSS REFERENCE TO RELATED APPLICATIONS

The present application is a U.S. National Phase Application pursuant to 35 U.S.C. §371 of International Application No. PCT/EP2014/057790 filed Apr. 16, 2014, which claims priority to European Patent Application No. 13164760.4 filed Apr. 22, 2013. The entire disclosure contents of these applications are herewith incorporated by reference into the present application.

FIELD OF INVENTION

An aspect of the present invention relates to a supplemental device for use with an injection device and relates particularly, but not exclusively, to a supplemental device for use with an injection device that is used to inject medicament such as insulin. Another aspect of the present invention relates to a method of operation of such a supplemental device. A further aspect of the present invention relates to a computer program for controlling a supplemental device to perform the foregoing method.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses that are administered. Supplemental devices may be used to record information about the various times at which insulin doses are administered and the quantity of insulin administered during each such dose.

Problems may arise however when a patient does not keep a record of what type of insulin they are using, and in more serious cases when a patient uses the wrong type of insulin. Aspects of the present invention address the foregoing.

Colour detection is disclosed in the prior art, for instance in WO2011/117212 and US2011/0238017.

SUMMARY

According to an aspect of the present invention there is provided a supplemental device for use with an injection device, the supplemental device comprising:
    a plurality of light sources each being configured to illuminate a surface portion of an injection device, in use, with light of a different wavelength;
    at least one sensor for generating sensor outputs indicative of the respective intensities of light of different wavelengths reflected from the surface portion; and
    a processor for:
        controlling the plurality of light sources to illuminate the surface portion with light of first to third different wavelengths;
        obtaining first to third values for sensor outputs corresponding to the first to third different wavelengths respectively;
        performing one or more calculations using at least the first and second values to provide one or more further values; and
        using the third value and the or each further value, but not the first and second values, to determine a property of the injection device.

This enables properties of injection devices to be determined by analysing reflection characteristics of a surface portion, or a part thereof, provided on such injection devices.

The supplemental device may comprise a connector configured to attach the supplemental device to an injection device in use;

The supplemental device may comprise light sources each being configured to generate light of a different wavelength which in use can be directed out of the supplemental device onto a surface portion of the injection device;

The or each calculation may comprise a division in which one of A and B is in the numerator and at least one of A and B is in the denominator, wherein A corresponds with the first value and B corresponds with the second value.

The division may comprise A/B.

The division may comprise A/(A+B). Advantageously, this minimises the effects of temperature drift imparted by the light source which emits light of the first wavelength for generating the first value. This can be particularly useful when that light source is a red LED because red LEDs are generally more susceptible to temperature drift than LEDs of colours such as blue and green.

The or each calculation may comprise a division in which C is in the denominator, wherein C corresponds with the third value.

One calculation may comprise A/(A+B+C) and another calculation may comprise B/(A+B+C).

Light of the first wavelength may be red, blue or green and light of the second wavelength may be another of red, blue or green.

Light of the first wavelength may be red, light of the second wavelength may be blue and light of the third wavelength may be green.

The processor may be configured to control the plurality of light sources to illuminate the surface portion with light of the first to third wavelengths for first to third exposure times respectively such that when the colour of the surface portion is neutral the first to third obtained values have substantially predetermined amounts. For instance, the processor may be configured to control the plurality of light sources to illuminate the surface portion with light of the first to third wavelengths for first to third exposure times respectively such that when the colour of the surface portion is grey the first to third obtained values have substantially predetermined amounts.

This minimises the total amount of time for which the light sources are activated in use, thereby reducing power consumption.

Using the third value and the or each further value to determine a property of the injection device may involve comparing the third value, or an additional value determined therefrom, and the or each further value with a record which associates a property of the injection device with respective ranges of such values.

The property of the injection device may be the type of injection device or the type of substance contained within the injection device.

According to another aspect of the present invention there is provided a method comprising a processor:

controlling a plurality of light sources to illuminate a surface portion of an injection device with light of first to third wavelengths, each light source being configured to emit light of a different wavelength;

obtaining first to third values for sensor outputs, generated by at least one sensor, that are indicative of the intensity of light of the first to third wavelengths reflected from the surface portion respectively;

performing one or more calculations using at least the first and second values to provide one or more further values; and using the third value and the or each further value, but not the first and second values, to determine a property of the injection device.

According to a further aspect of the present invention there is provided a computer program comprising machine readable instructions that when executed by a supplemental device comprising a plurality of light sources, at least one sensor and at least one processor, controls it to perform the foregoing method.

DETAILED DESCRIPTION

In the following, embodiments of the present invention will be described in the context of a supplemental device for determining an amount of dose dialled, or an amount of dose dispensed, by an injection device. Such a supplemental device may be provided with optical character recognition (OCR) functionality for making such a determination. The present invention is however not limited to such application and may equally well be deployed with supplemental devices of other kinds, for example a supplemental device that merely displays a dialled dose amount in larger format than it appears on the number sleeve of an injection device.

Figure 1:
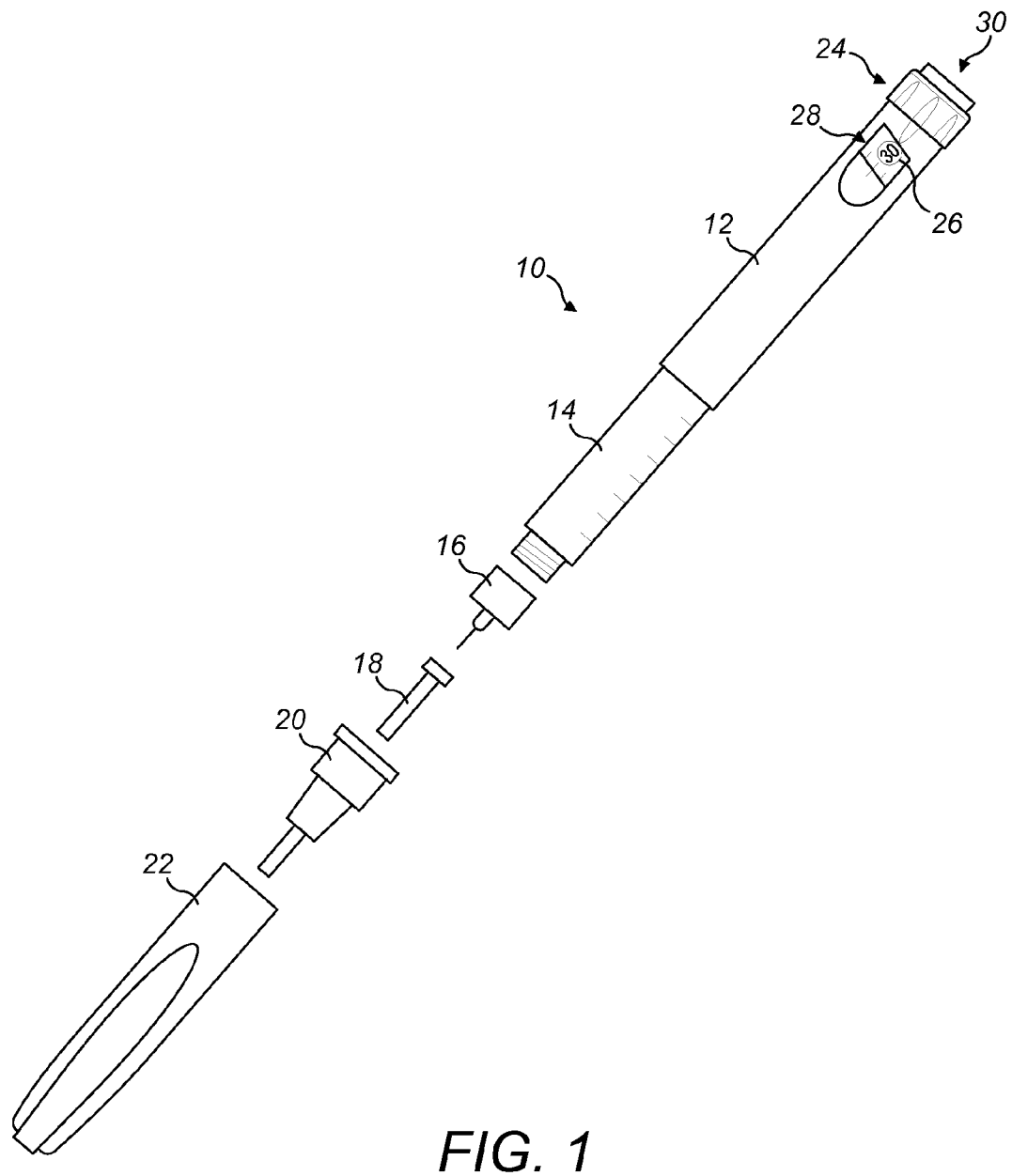
FIG. 1 is a schematic view of an exemplary injection device.

FIG. 1 is an exploded view of an injection device 10, which may for instance represent the Solostar™ injection pen sold by Sanofi.

The injection device 10 of FIG. 1 is a pre-filled, disposable injection pen that comprises a housing 12 and contains an insulin container 14, to which a needle 16 can be affixed. The needle 16 is protected by an inner needle cap 18 and an outer needle cap 20, which in turn can be covered by a cap 22. An insulin dose to be ejected from injection device 10 can be selected by turning the dosage knob 24 (this act may be referred to as dialling an insulin dose). A marker comprising a number 26 indicative of the selected dose (the dialled dose) is displayed via dosage window 28 in multiples of International Units (IU) for instance. An example of a dialled dose displayed in the dosage window 28 may be 30 IUs, as shown in FIG. 1.

The numbers 26 displayed in the dosage window 28 are printed on a sleeve (known as the number sleeve 17) contained in the housing 12 and which mechanically interacts with a piston inside the insulin container 14. When needle 16 is inserted into the skin of a patient and the injection button 30 is pushed, an amount of insulin corresponding to the dialled quantity displayed in the display window 28 is ejected from the injection device 10. During the course of the injection, as insulin leaves the injection device 10, the number sleeve 17 rotates. This causes the number 26 displayed in the dosage window 28 to change in accordance with the dialled amount of insulin yet to be dispensed. In other words, during the course of an injection the numbers 26 that successively align with the dosage window 28 are caused to count down.

Figure 2:
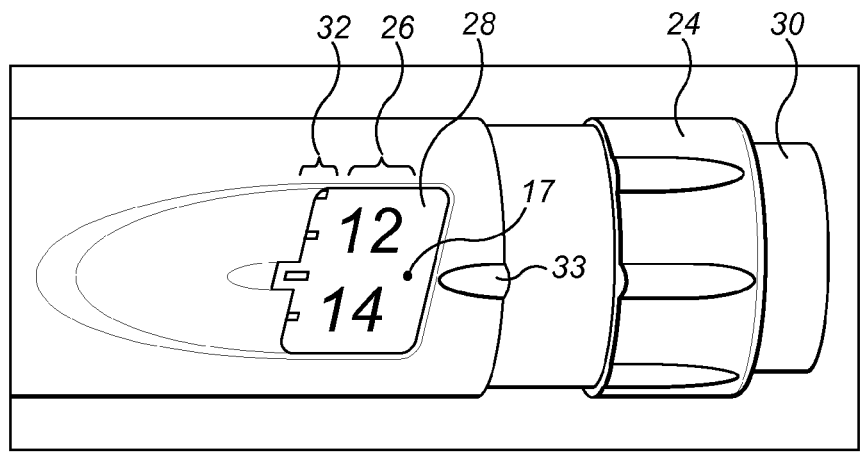
FIG. 2 is an enlarged view of an end of the injection device in FIG. 1.

FIG. 2 shows the dosage window 28 after 17 IUs of insulin have been delivered from the injection device 10 during the course of the injection in the preceding paragraph.

Figure 3:
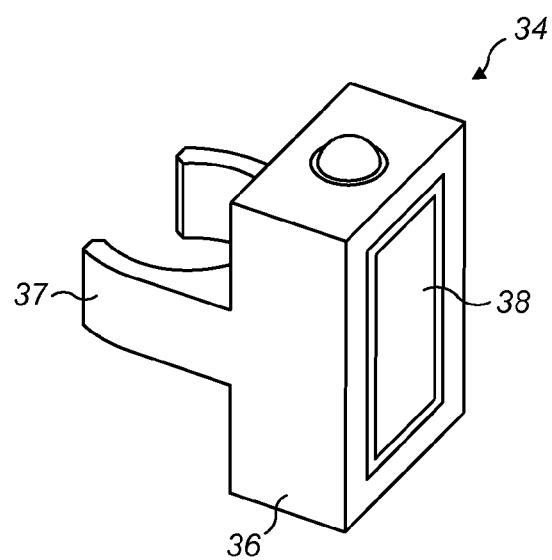
FIG. 3 is a schematic view of a supplemental device according to one embodiment of the present invention.

FIG. 3 is a schematic illustration of a supplemental device 34 which may be releasably attached to an injection device such as the one depicted in FIG. 1. The supplemental device 34 comprises a housing 36 which is provided with a mating unit, coupling unit or connector 37 for embracing the housing 12 of an injection device 10. In particular the connector 37 may be configured to snap-fit onto the housing 12 of an injection device 10 in such a way that the device 34 can be subsequently removed therefrom. The connector 37 need not however be of the snap-fit variety and other arrangements may alternatively be suitable for coupling the supplemental device 34 to an injection device.

Figure 4:
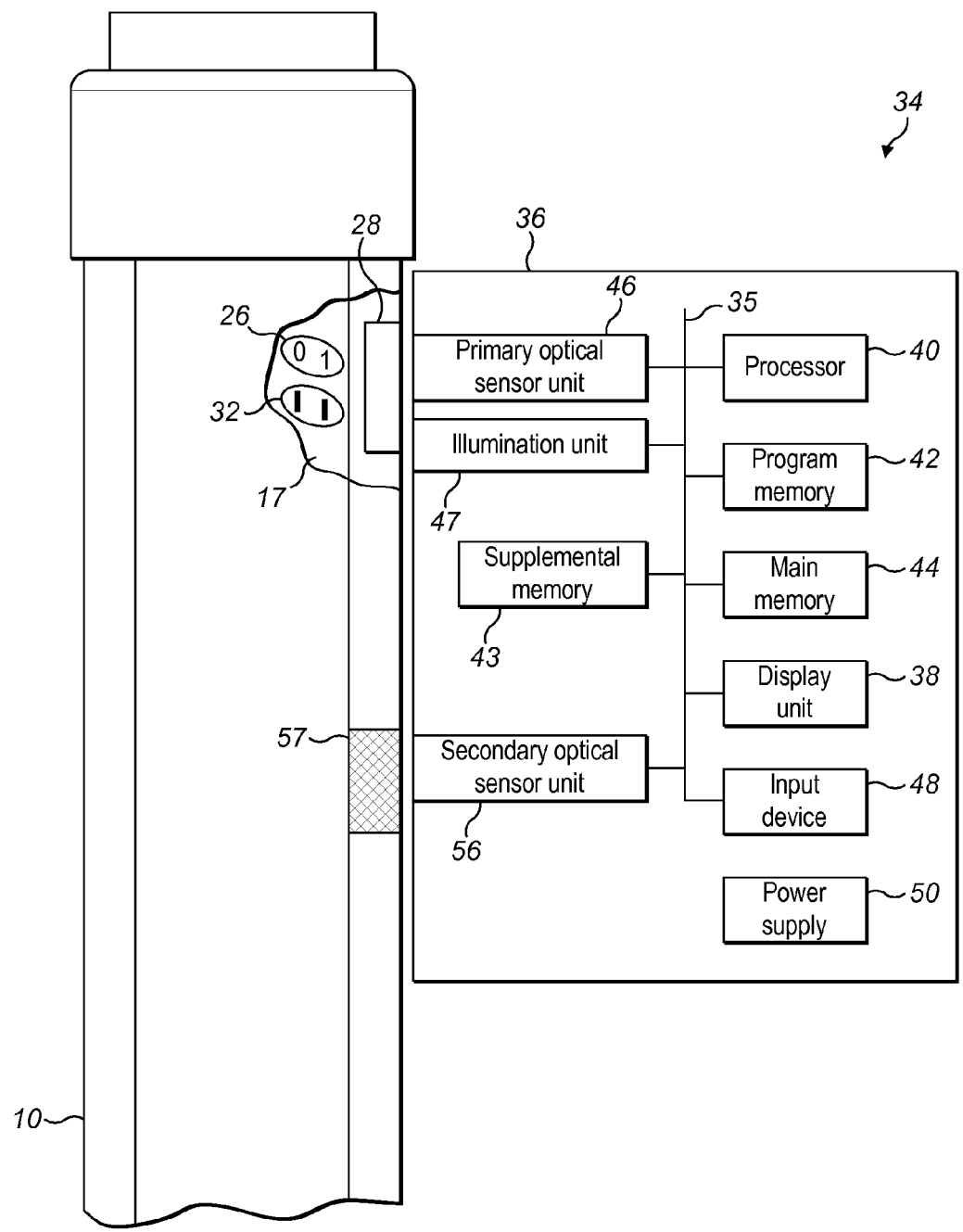
FIG. 4 is a schematic internal view of the supplemental device in FIG. 3.

When coupled to an injection device 10, the supplemental device 34 obstructs the dosage window 28 (as in FIG. 4). The supplemental device 34 contains at least one optical sensor for gathering information from the injection device 10. In particular the optical sensor(s) is(are) caused to gather information indicative of what is displayed in the dosage window 28. This gathered information is then capable of being processed for generating a dose history database. Such a dose history database may include records containing information about the various times at which insulin doses are administered and the quantity of insulin administered during each dose. The gathered information may also be processed for the purpose of displaying numbers 26 aligned with the dosage window 28 in larger format, for example by displaying numbers on a display unit which are larger than those provided on the number sleeve 17. This improves the readability of the amount of dose dialled or, in the case of an injection, the dialled dose amount yet to be delivered.

FIG. 4 illustrates an internal schematic view of the supplemental device 34 in a state where it is coupled to an injection device 10.

Within the housing 36 of the supplemental device 34, a variety of components are located and coupled together by a system bus 35. One such component includes a processor 40. Program memory 42 and main memory 44 are also coupled to the system bus 35. The processor 40 executes program code (e.g. software or firmware) stored in the program memory 42 and uses the main memory 44 to store intermediate results. The supplemental device 34 also comprises a supplemental memory 43 for storing the aforementioned dose history database. Program memory 42 may for instance be non-volatile memory such as Read-Only Memory. Main memory 44 may for instance be a volatile memory such as Random Access Memory, DRAM or SDRAM and supplemental memory 43 may for instance be Flash memory or an EEPROM or may comprise a memory card coupled to the system bus 35 via an interface such as a USB-type connection.

A primary optical sensor unit 46, also coupled to the system bus 35, is used to generate signals containing information indicative of what is displayed in the dosage window 28. The processor 40 may use these signals to determine delivered doses and generate the dose history database. The processor 40 may achieve this by executing an optical character recognition application to determine, from signals sent by the primary optical sensor unit 46, which number(s) 26 is(are) aligned with the dosage window 28. On the basis of such information the processor 40 then determines how much insulin has been dialled or, in the case of an injection, the dialled amount of insulin that remains to be delivered (or has already been delivered during the course of the injection).

Other components which may be coupled to the system bus 35 include an illumination unit 47, a display unit 38 and an input device 48. Such an illumination unit 47 may include one or more LEDs and may be controlled by the processor 40 to illuminate information displayed in the dosage window 28. An input device 48 (for example, a keypad) may be utilised by a user to interact with the supplemental device 34. Such an input device 48 may for instance be used to select one or more options displayed on a display unit 38. In some embodiments a display unit 38 may be provided with touch-screen functionality thus enabling it to function as both an output device and the input device 48.

A power supply source 50 (for example a battery) is for powering the various components of the supplemental device 34.

In some embodiments, the primary optical sensor unit 46 may comprise a camera and the processor 40 may cause a display unit 38 to show information, e.g. images, that represent the number sleeve 17 as it appears in the field of view of the camera.

Regardless of the particular combination of features provided, a supplemental device 34 according to the present invention further comprises a secondary optical sensor unit 56 coupled to the system bus 35. The processor 40 uses the secondary optical sensor unit 56 to determine characteristics of a surface portion 57 located on an injection device 10. The surface portion 57 may comprise a label or a part of the outer casing of the injection device 10 for instance. The surface portion 57 may thus be fixed, adhered or printed onto the injection device 10 or may comprise an integral part of the outer casing of the injection device 10. This is useful because injection devices 10 having different properties may be provided with different kinds of surface portions 57. For example, injection devices 10 containing different types of medicament (e.g. different types of insulin) may have different coloured surface portions 57. A supplemental device 34 of the present invention is thus able to determine what type of medicament an injection device 10 contains by analysing characteristics of its surface portion 57 or a part of the surface portion 57, for instance a part of a label that includes details of the injection device 10 such as brand information.

As will be explained in more detail below, the processor 40 causes the secondary optical sensor unit 56 to illuminate the surface portion 57 with light of different wavelengths. The secondary optical sensor unit 56 generates signals indicative of the intensity of light, of each respective wavelength, reflected by the surface portion 57. These signals are then used by the processor 40 to determine a property of the injection device 10. This is enabled by the processor 40 comparing the reflection characteristics of the surface portion 57 with one or more records, each of which associates a different property of an injection device with a respective reflection response. Different coloured surface portions 57 reflect different amounts of light across a spectrum of different wavelengths. Thus by determining the reflection characteristics of a surface portion 57 having a particular colour, a property associated with that colour in one of the aforementioned records can be determined. An example of one such property may be an injection device type or a medicament type.

As already mentioned, an implementation of the present invention is to distinguish medical devices having different coloured surface portions 57, e.g. depending on the kind of medication they contain. Alternatively, the surface portions 57 could be coloured differently depending on the type of insulin the respective devices contain.

For example, injection devices 10 containing short-acting insulin may be provided with a first coloured, e.g. red coloured, surface portion 57 whereas injection devices 10 containing long-acting insulin may be provided with a second coloured, e.g. blue coloured, surface portion 57. A first record which associates short-acting insulin with reflection characteristics of the first colour, the colour red in this example, and a second record which associates long-acting insulin with reflection characteristics of the second colour, the colour blue in this example, may be accessed by the processor 40 for determining what type of insulin is contained within a particular injection device 10. More specifically, the reflection characteristics of the surface portion 57 of a particular injection device 10 are compared with those in the foregoing records. This enables the processor 40 to determine what insulin type has been associated with the colour of the surface portion 57. If the surface portion 57 is blue, for instance, then the processor 40 determines that the injection device 10 contains long-acting insulin.

It will be appreciated that injection devices containing other types of insulin or other types of medicament may be provided with different coloured surface portions. Following on from the example in the foregoing paragraph such colours should be other than red or blue. Corresponding records associating reflection characteristics of the various surface portion colours with respective types of insulin or other medicament may be provided for enabling a processor to determine what substance is contained by an injection device upon analysing reflection characteristics of its surface portion (or a part thereof).

Details of the secondary optical sensor unit 56 will now be explained in more detail with reference to FIG. 5.

The secondary optical sensor unit 56 comprises a plurality of light sources 58 such as LEDs for illuminating a surface portion 57 of an injection device in use. Each light source 58 may be configured to emit light of a different wavelength. For example the first, second and third light sources 58$a$, 58$b$, 58$c$ in FIG. 5 are configured to emit first, second and third wavelengths $\lambda_1$, $\lambda_2$, $\lambda_3$ of light respectively. However, a plurality of light source groups may be provided instead, the light sources in each group being configured to emit light of the same wavelength.

Light of the first wavelength $\lambda_1$ emitted by the first light source 58$a$ may be red, blue or green. Light of the second wavelength $\lambda_2$ emitted by the second light source 58$b$ may be another of red, blue or green. Light of the third wavelength $\lambda_3$ emitted by the third light source 58$c$ may be the remaining of red, blue or green.

In some embodiments, light of the first wavelength $\lambda_1$ is red, light of the second wavelength $\lambda_2$ is blue and light of the third wavelength $\lambda_3$ is green. Throughout this specification, red light has a wavelength between approximately 620 nm and 740 nm, blue light has a wavelength between approximately 450 nm and 495 nm and green light has a wavelength between approximately 520 nm and 570 nm.

The examples of the first to third wavelengths $\lambda_1$, $\lambda_2$, $\lambda_3$ outlined in the foregoing paragraph are merely exemplary. Such wavelengths may be of any value so long as they are different from one another. Additionally, the emissions of a light source 58 may not be solely at one discrete frequency but may instead be spread over a relatively narrow band of frequencies, which may overlap to some extent with the band of another light source 58. Also, one or more of the first to third wavelengths $\lambda_1$, $\lambda_2$, $\lambda_3$ may be outside the visible spectrum and could be infrared or ultraviolet for instance.

Referring again to FIG. 5, the secondary optical sensor unit 56 further comprises a sensor 60 for generating sensor outputs. Such sensor outputs are indicative of the respective intensities of light of different wavelengths reflected from the surface portion 57. For instance following an exposure time, during which reflected light of a particular wavelength is incident on the sensor 60, the sensor 60 generates a signal indicative of the intensity of reflected light of that particular wavelength on the sensor 60 during that particular exposure time. In use, different wavelengths of light are caused to become incident on the sensor 60 for respective exposure times. The sensor 60 generates signals indicative of the intensity of reflected light of each particular wavelength on the sensor 60 during the respective exposure times.

Figure 5:
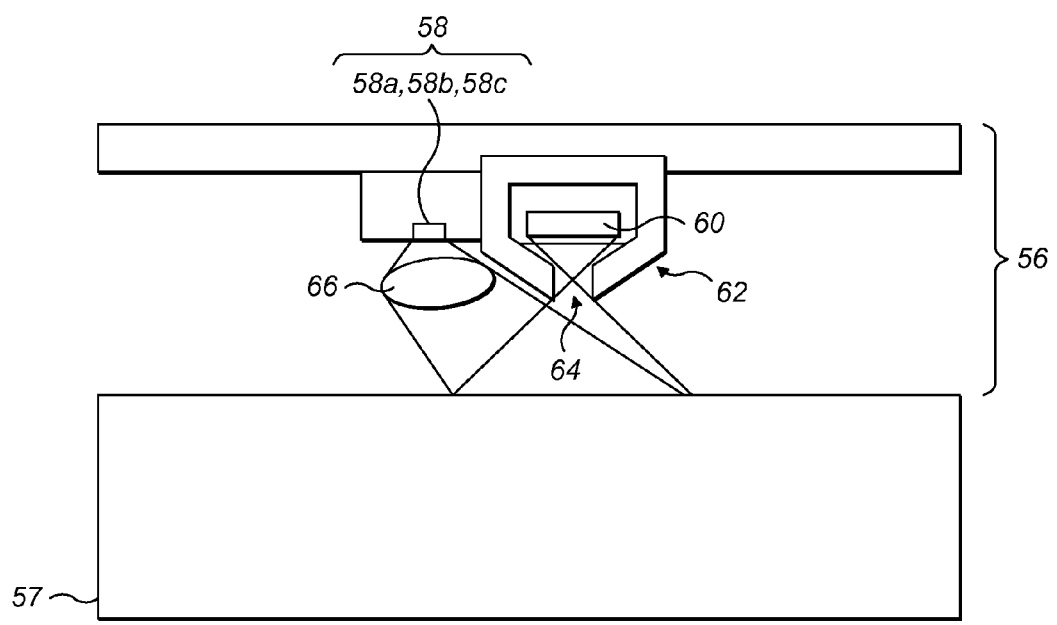
FIG. 5 is a schematic cross-sectional diagram of a secondary optical sensor unit.

In the example of FIG. 5, the processor 40 causes the first to third light sources 58a to 58c to respectively emit light of the first to third wavelengths $\lambda_1$ to $\lambda_3$ for respective exposure times $t_1$ to $t_3$. The light sources 58a to 58c are controlled to sequentially emit light of the first to third wavelengths $\lambda_1$ to $\lambda_3$. Therefore following a first exposure time $t_1$, during which reflected light of the first wavelength $\lambda_1$ is incident on the sensor 60, the sensor 60 generates a first signal S1 (described in the next paragraph). Following a second exposure time $t_2$, during which reflected light of the second wavelength $\lambda_2$ is incident on the sensor 60, the sensor 60 generates a second signal S2. Furthermore following a third exposure time $t_3$, during which light of the third wavelength $\lambda_3$ is incident on the sensor 60, the sensor 60 generates a third signal S3.

The first signal S1 mentioned in the foregoing paragraph is indicative of the intensity of reflected light of the first wavelength $\lambda_1$ incident on the sensor 60 during the first exposure time $t_1$. Similarly the second signal S2 is indicative of the intensity of reflected light of the second wavelength $\lambda_2$ incident on the sensor 60 during the second exposure time $t_2$. The third signal S3 is indicative of the intensity of reflected light of the third wavelength $\lambda_3$ incident on the sensor 60 during the third exposure time $t_3$.

A supplemental device 34 of the present invention is calibrated such that if the surface portion 57 (or at least the part thereof from which light reflects onto the sensor 60) is a neutral colour (e.g. grey) then the respective signals generated by the sensor 60, in response to detecting light of the different wavelengths, are substantially similar. More specifically in such circumstances the respective signals generated by the sensor 60, which are indicative of the intensity of reflected light of each particular wavelength on the sensor 60 during the respective exposure times, are substantially similar.

In the example in FIG. 5, the supplemental device 34 is configured such that if the surface portion 57 (or at least the part thereof from which light reflects onto the sensor 60) is a neutral colour (e.g. grey) then the first to third signals S1 to S3 generated by the sensor 60 in use will be substantially similar. Such signals S1 to S3 are deemed to be substantially similar if they are indicative that during first to third exposure times $t_1$ to $t_3$ the intensity of reflected light of the first to third respective wavelengths $\lambda_1$ to $\lambda_3$ on the sensor 60 is substantially similar.

Calibrating a supplemental device 34 to perform in this manner involves altering the duration of one or more of the exposure times of light of the respective wavelengths (exposure times $t_1$ to $t_3$ in the example of FIG. 5). The respective durations of the calibrated exposure times are stored by the supplemental device 34, for example in the program memory 42. The supplemental device 34 utilises these calibrated exposure time durations when in use for the respective exposure times of light of different wavelengths. Advantageously, calibrating a supplemental device 34 in this way minimises the total amount of time for which the light sources 58 are activated in use. This reduces the power consumption of the supplemental device 34, thereby prolonging battery life.

Referring again to FIG. 5, the secondary optical sensor unit 56 in a supplemental device 34 of the present invention is further provided with a screen 62 (or light proof cover). This screen is opaque to light of the wavelengths emitted by the light sources 58. For example, in FIG. 5 the screen 62 is opaque to light of at least the first, second and third wavelengths $\lambda_1$, $\lambda_2$, $\lambda_3$. The screen 62 prevents light emitted by the light sources 58 becoming directly incident on the sensor 60. An aperture 64 is defined by the screen 62 in the field of view of the sensor 60. In use, the surface portion 57 of an injection device 10 is caused to be aligned with both the aperture 64 and the sensor 60 as shown in FIGS. 4 and 5. This occurs when the connector 37 (see FIG. 3) is coupled to the injection device 10. Such alignment provides that the surface portion 57 (or at least a section of the surface portion) is in the field of view of the sensor 60, in use. The light sources 58 are not aligned with the sensor 60 and the aperture 64. This provides that the light sources 58 are not in the field of view of the sensor 60. Thus when the processor 40 causes the light sources 58 to emit light, only light emitted by the light sources 58 that is reflected from the section of the surface portion 57 in the field of view of the sensor 60 is detected.

Figure 6:
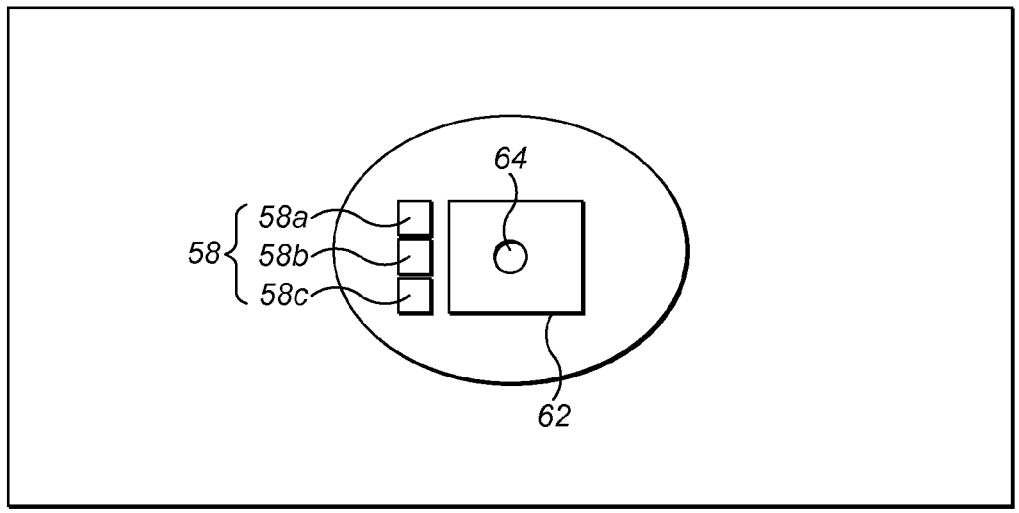
FIG. 6 is a schematic diagram of the underside of the secondary optical sensor unit in FIG. 5.

FIG. 6 shows that respective light sources (e.g. those denoted 58a, 58b and 58c) may be arranged adjacent to one another for example in a line. Respective light sources may however be distributed around the screen 62. For example one or more light sources may be located to the left of the screen 62 in FIG. 6 and one or more other light sources may be located to the right of the screen 62 in FIG. 6. Also, in some embodiments light sources may be arranged in a ring, square, rectangle or triangle around the screen 62.

One or more lenses 66 may be provided for focussing light emitted by the light sources 58 onto the surface portion 57 (or a section thereof in the field of view of the sensor 60), although this is not necessary. Furthermore one or more lenses (not shown) may be provided for focussing light reflected by the surface portion 57 onto the sensor 60, however this is also not necessary. Advantageously, this improves the reliability of the reflection response analysis capable of being performed by a supplemental device 34 of the present invention because light that has not been reflected from the surface portion 57 cannot influence signals generated by the sensor 60. In particular, a supplemental device 34 of the present invention is configured such that, in use, only light emitted from the light sources 58 and reflected by the surface portion 57 is able to become incident on the sensor 60.

How the secondary optical sensor unit 56 is used by the processor 40 to determine a property of an injection device 10 will now be explained with particular reference to the example in FIG. 5. The processor 40 controls the first, second and third light sources 58a, 58b, 58c sequentially to illuminate the surface portion 57 with light of first, second and third wavelengths $\lambda_1$, $\lambda_2$, $\lambda_3$ respectively for respective calibrated exposure times $t_1$, $t_2$, $t_3$. Upon such illumination the sensor 60 generates first, second and third signals S1, S2 and S3 respectively. These first to third signals S1 to S3 are (as aforementioned) indicative of the intensity of reflected light incident on the sensor 60 during the respective exposure times.

The processor 40 uses the first to third signals S1 to S3 to obtain first to third respective values A to C. In other words, the processor 40 assigns a numerical value to each of the first to third signals S1 to S3. The respective magnitudes of the first to third values A to C are proportional to a property of the first to third respective signals S1 to S3 that changes in accordance with the intensity of reflected light incident on the sensor 60 during a particular exposure time.

In the example that the sensor 60 is a photodiode for instance, the magnitude of an output voltage signal generated by the photodiode depends on the intensity of incident light during a particular exposure time. Thus when light of the first wavelength $\lambda_1$ for example is incident on the photodiode for an exposure time $t_1$, if the magnitude of the output voltage signal S1 is low then the corresponding first value A obtained by the processor 40 will be low also. However if the magnitude of the output voltage signal S1 generated is higher due to an increased intensity of light of the first wavelength $\lambda_1$ during the exposure time $t_1$, then the first value A obtained by the processor 40 will also be higher. The same applies in respect of the second and third values B and C obtained using second and third output voltage signals S2 and S3 generated when the photodiode is illuminated with light of the second and third wavelengths $\lambda_2$ and $\lambda_3$ respectively.

The first to third values A to C might be indicative of power per unit area (W/m$^2$). The first value A might be indicative of the power per unit area of light of the first wavelength $\lambda_1$ on the sensor 60 during a first exposure time $t_1$. Similarly the second and third values B and C might be indicative of the power per unit area of light of the second and third respective wavelengths $\lambda_2$ and $\lambda_3$ on the sensor 60 during second and third respective exposure times $t_2$ and $t_3$. The first to third values A to C might not however be indicative of power per unit area and might instead be indicative of another quantity, provided that the first to third values A to C are indicative of the same quantity. For example the first to third values A to C may be indicative of the total amount of electromagnetic energy (Joules) incident on the sensor 60 during respective exposure times $t_1$ to $t_3$.

The processor 40 performs a calculation using the first and second values A and B to provide a fourth value D. The processor 40 does not use the third value C when performing this calculation. Calculating the value of D comprises determining the output of a function f(A, B). Thus mathematically f(A, B)=D, wherein f(A, B) may comprise at least a division in which A is in the numerator and B is in the denominator. For example calculating the value of D may involve determining at least the value of A/B or A/(A+B).

The processor 40 also performs another calculation in which the third value C is used to provide a fifth value E. Calculating the value of E comprises determining the output of a function f(C). Thus mathematically f(C)=E, wherein f(C) comprises one or more calibration factors which will be discussed later.

Having determined the fourth and fifth values D and E the processor 40 determines a property of the injection device 10 it is analysing. This is enabled by the processor 40 comparing the determined fourth and fifth values D and E with a list of records. These records respectively associate different information with different combinations of predetermined fourth and fifth values D and E.

The predetermined fourth and fifth values D and E in a particular record are those that the processor 40 determines if the surface portion 57 of an injection device 10 (or at least the part thereof in the field of view of the sensor 60) is a particular colour. This is how providing an injection device 10 with a surface portion 57 of a particular colour enables a supplemental device 34 to determine a property of the injection device 10. More specifically, providing the surface portion 57 with a particular colour results in the processor 40 determining a particular combination of fourth and fifth values D and E that are only determined when the analysed surface portion 57 is that particular colour. Comparing these values with the one or more records accessible by the processor 40 enables the processor to determine which particular property has been associated with those particular fourth and fifth values D and E.

In practice, providing the surface portion 57 of an injection device with a particular colour may not result in the processor 40 determining particular fourth and fifth values D and E exactly. Instead, such values may only be determined within a range of accuracy that is influenced by the manufacturing tolerances of the supplemental device assembly process, and also, the efficiency of the various components thereof for example the sensor 60 and light sources 58. As such the records previously mentioned may associate predetermined ranges of fourth and fifth values D and E with particular injection device properties (instead of associating exact values with injection device properties).

It will be appreciated that information indicative of different injection device types may be included in respective records. In other words, different injection device types may be associated with different combinations of predetermined fourth and fifth values D and E (or ranges thereof). In this implementation, different types of injection devices 10 may be provided with different coloured surface portions 57 for enabling a supplemental device 34 to determine the type of injection device 10.

It will also be appreciated that information indicative of different types of medicament (e.g. different types of insulin) may be included in respective records. In other words, different types of medicament may be associated with different combinations of predetermined fourth and fifth values D and E (or ranges thereof). In this implementation, injection devices 10 may be provided with different coloured surface portions 57 for enabling a supplemental device 34 to determine the type of medicament contained within the injection device 10.

Information concerning the type of medicament which a person injects themselves with may be stored in the aforementioned dose history database. Also, a supplemental device 34 may be configured to alert a user when an injection device 10 is determined to contain other than a pre-specified type of medicament. Such an alert may comprise the sounding on an audible alarm or the presentation of a visual indication on a display unit.

Figure 7:
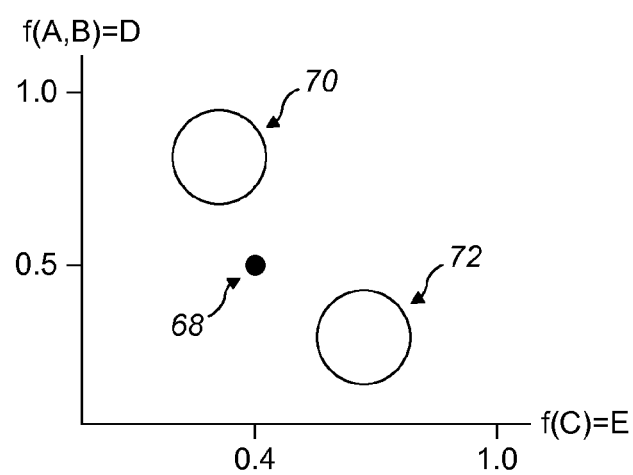
FIG. 7 is a graphical representation of fourth and fifth values that may be determined by the supplemental device in FIGS. 3 and 4.

FIG. 7 is a graphical representation of the foregoing. The vertical axis represents possible magnitudes of the fourth value D, which is the output of the function f(A, B). The horizontal axis represents the possible magnitudes of the fifth value E, which is the output of the function f(C). Since different coloured surface portions 57 are associated with different fourth and fifth values D and E, different coloured surface portions 57 are associated with different locations in the space shown in FIG. 7.

In the previous discussion regarding records it was stated that respective records may associate predetermined ranges of fourth and fifth values D and E with particular injection device properties. This is represented graphically in FIG. 7. For example, if the location associated with a particular coloured surface portion 57 is determined to be in the area 70 then the injection device 10 having that surface portion 57 is determined to have a particular property. However, if the location associated with a particular coloured surface portion 57 is determined to be in the area 72 then the injection device 10 having that surface portion 57 is determined to have another property.

The shape of an area associated with a particular property, such as those denoted 70 and 72 in FIG. 7, may define any shape. For instance one or more of the areas 70, 72 in FIG. 7 could define a square, rectangle, polygon, circle or oval for instance. Consider the example in which an area defines a square that extends between 0.9 and 1.0 on both the vertical and horizontal axes in FIG. 7. In this example the combination of D=0.9 to 1.0 and E=0.9 to 1.0 is associated with short-acting insulin. If the respective fourth and fifth values D and E of a particular surface portion 57 are each determined to be within the range 0.9 to 1.0, then the injection device 10 having that surface portion is determined to contain short-acting insulin.

Further configuration of a supplemental device 34 according to the present invention is required such that different supplemental devices 34 determine substantially similar fourth and fifth values D and E for a surface portion 57 of the same colour. Graphically this means that further configuration is required such that different supplemental devices 34 determine surface portions 57 of the same colour to be associated with substantially similar locations in FIG. 7.

How such configuration is achieved will now be explained. A supplemental device 34 of the present invention is configured such that if the surface portion 57 is a neutral colour (e.g. grey), the processor 40 determines the fourth and fifth values D and E to have predetermined magnitudes. The same occurs provided at least the part of the surface portion 57, from which light reflects onto the sensor 60, is neutral in colour.

The function f(A, B) used to determine the fourth value D may be such that the possible values of D range between 0 and 1. This function f(A, B) may also be such that if the surface portion 57 (specifically the part thereof from which light reflects onto the sensor 60) is a neutral colour (e.g. grey) the value of D is determined to be substantially 0.5.

A neutral coloured surface portion, for example a particular shade of grey, may have a reflectance of approximately 40% across all spectral ranges. In the foregoing example where the function f(A, B) comprises A/(A+B) the values of A and B will be substantially the same if the surface portion 57 is this colour. This is because (as already mentioned) the respective magnitudes of the first to third values A to C are proportional to a property of the first to third respective signals S1 to S3 that changes in accordance with the intensity of reflected light incident on the sensor 60 during a particular exposure time. Thus if the reflectance of the surface portion 57 is approximately 40% for light of the first to third wavelengths $\lambda_1$ to $\lambda_3$ then the respective values of A to C will be substantially similar. This provides that the fourth value D determined by calculating A/(A+B) will be substantially 0.5. Advantageously, if the function f(A, B) comprises A/(A+B) this minimises the effects of temperature drift imparted by the first light source 58a that emits light of the first wavelength for $\lambda_1$ for generating the first value A. This can be particularly useful where the first light source 58a is a red LED, because red LEDs are generally more susceptible to temperature drift than LEDs of colours such as blue and green.

The function f(C) used to determine the fifth value E may be such that the possible values of E also range between 0 and 1. For a neutral coloured surface having a reflectance of approximately 40% across all spectral ranges, the reflectance of light of the third wavelength $\lambda_3$ used to obtain the third value C will be 40% if the surface portion 57 (or at least the part thereof from which light reflects onto the sensor 60) is this colour. Such a colour may be the particular shade of grey mentioned in the previous paragraph. Calibration factors in the function f(C) may be set such that in this situation the value of E output from the function f(C) is substantially 0.4. These calibration factors are stored by the supplemental device 34, in the program memory 42 for example.

Consider a scenario in which a supplemental device 34 is calibrated in accordance with the previous two paragraphs. Such calibrated supplemental device 34, when coupled to an injection device 10 having a surface portion 57 that is of a shade of grey with a reflectance of approximately 40% across all spectral ranges, will determine the fourth and fifth values D and E to be those associated with the calibration location denoted 68 in FIG. 7.

In view of the foregoing it will be appreciated that in determining a property of an injection device 10 based on reflection characteristics of a surface portion 57, a supplemental device 34 according to the present invention could also utilize a three dimensional system which comprises two colour parameters D1 and D2 and one brightness parameter E. The two colour parameters D1 and D2 will be calculated as a function of (A, B, C). For example, D1=A/(A+B+C) and D2=B/(A+B+C). The brightness parameter E will be calculated similar to the foregoing as a function of C, E=f(C).

The heretofore described operation of the second optical sensor unit 56 is realised by the processor 40 operating in accordance with instructions contained in an operation application stored in the program memory 42. Relevant calibration information such as the calibrated exposure times (e.g. $t_1$ to $t_3$) and the aforementioned calibration factors may be accessed by the processor 40 operating in accordance with instructions contained in the operation application.

It will be appreciated that the above described embodiments are purely illustrative and are not limiting on the scope of the invention. Other variations and modifications will be apparent to persons skilled in the art upon reading the present application.

For example, in some embodiments the secondary optical sensor unit 56 comprises a plurality of different sensors 60 (for example, a plurality of photodiodes). However each such sensor is additionally provided with a filter configured to filter incident light such that only light of a particular wavelength (or range of wavelengths) is detected by the sensor. In such an embodiment the secondary optical sensor unit 56 comprises one or more sensors configured to detect reflected light of the first wavelength $\lambda_1$. The secondary optical sensor unit 56 also comprises one or more sensors configured to detect reflected light of the second wavelength $\lambda_2$. The secondary optical sensor unit 56 further comprises one or more sensors configured to detect light of the third wavelength $\lambda_3$. In this embodiment the processor 40 causes the first to third light sources 58a to 58c (or groups thereof) to concurrently emit light of the first to third wavelengths $\lambda_1$ to $\lambda_3$ onto the surface portion 57 in use. This provides that first to third signals similar to those heretofore described (i.e. first to third signals S1 to S3) are generated concurrently.

In the embodiment outlined in the previous paragraph, although the respective exposure times for light of different wavelengths elapse concurrently, such exposure times may be of different durations. This is for calibration purposes. Specifically, this is such that if a surface portion 57 (or at least the part thereof from which light reflects onto the sensors) is a neutral colour (e.g. grey), then the signals generated by the respective sensors in response to detecting light of the different wavelengths are substantially similar. More specifically in this situation the signals generated by the respective sensors, which are indicative of the intensity of reflected light of respective wavelengths during respective exposure times, are substantially similar.

Lastly, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. A supplemental device comprising:
 a connector configured to attach the supplemental device to an injection device in use;
 a plurality of light sources each being configured to generate light of a different wavelength which in use can be directed out of the supplemental device onto a surface portion of the injection device;
 at least one sensor for generating sensor outputs indicative of the respective intensities of light of different wavelengths reflected from the surface portion in use; and
 a processor configured to:
  control the plurality of light sources to illuminate the surface portion with light of first to third different wavelengths;
  obtain first to third values for sensor outputs corresponding to the first to third different wavelengths respectively;
  perform one or more calculations using at least the first and second values to provide one or more further values; and
  use the third value and the or each further value, but not the first and second values, to determine a property of the injection device.

2. The supplemental device of claim 1, wherein the or each calculation comprises a division in which one of A and B is in the numerator and at least one of A and B is in the denominator, wherein A corresponds with the first value and B corresponds with the second value.

3. The supplemental device of claim 2, wherein the division comprises A/B.

4. The supplemental device of claim 2, wherein the division comprises A/(A+B).

5. The supplemental device of claim 2, wherein the or each calculation comprises a division in which C is in the denominator, wherein C corresponds with the third value.

6. The supplemental device of claim 5, wherein one calculation comprises A/(A+B+C) and another calculation comprises B/(A+B+C).

7. The supplemental device of claim 1, wherein light of the first wavelength is red, blue or green and light of the second wavelength is another of red, blue or green.

8. The supplemental device of claim 7, wherein light of the first wavelength is red.

9. The supplemental device of claim 7, wherein light of the second wavelength is blue and wherein light of the third wavelength is green.

10. The supplemental device of claim 1, wherein the processor is configured to control the plurality of light sources to illuminate the surface portion with light of the first to third wavelengths for first to third exposure times respectively such that when the colour of the surface portion is neutral the first to third obtained values have substantially predetermined amounts.

11. The supplemental device of claim 1, wherein the processor is configured to control the plurality of light sources to illuminate the surface portion with light of the first to third wavelengths for first to third exposure times respectively such that when the colour of the surface portion is grey the first to third obtained values have substantially predetermined amounts.

12. The supplemental device of claim 1, wherein using the third value and the or each further value to determine a property of the injection device involves comparing the third value, or an additional value determined therefrom, and the or each further value with a record which associates a property of the injection device with respective ranges of such values.

13. The supplemental device of claim 1, wherein the property of the injection device is the type of injection device or the type of substance contained within the injection device.

14. The supplemental device of claim 1, wherein the processor is configured to:
 determine the reflection characteristics of a surface portion of an injection device when attached thereto having a particular colour;
 compare the reflection characteristics of the surface portion with one or more records, each of which associates a different property of an injection device with a respective reflection response.

15. A method comprising a processor performing the steps of:
 controlling a plurality of light sources to respectively generate light of first to third wavelengths and causing said light to be directed out of a supplemental device onto a surface portion of an injection device attached to the supplemental device;
 obtaining first to third values for sensor outputs, generated by at least one sensor, that are indicative of the intensity of light of the first to third wavelengths reflected from the surface portion respectively;
 performing one or more calculations using at least the first and second values to provide one or more further values; and
 using the third value and the or each further value, but not the first and second values, to determine a property of the injection device.

16. A computer program comprising machine readable instructions that when executed by a supplemental device comprising a plurality of light sources, at least one sensor and at least one processor, controls it to perform the method of claim 15.

\* \* \* \* \*